United States Patent [19]

Epple

[11] Patent Number: 5,082,957
[45] Date of Patent: Jan. 21, 1992

[54] PREPARATION OF 1-AMINO-2-BROMO-4-HYDROXYAN-THRAQUINONE

[75] Inventor: Gerhard Epple, Weisenheim, Fed. Rep. of Germany

[73] Assignee: Basf Aktiengesellschaft, Ludwigshafen, Fed. Rep. of Germany

[21] Appl. No.: 437,660

[22] Filed: Nov. 17, 1989

[30] Foreign Application Priority Data

Dec. 14, 1988 [DE] Fed. Rep. of Germany ....... 3841988

[51] Int. Cl.$^5$ ............................................. C07C 97/24
[52] U.S. Cl. ............................................. 552/244
[58] Field of Search ................................... 552/244

[56] References Cited

U.S. PATENT DOCUMENTS

| | | | |
|---|---|---|---|
| 3,086,977 | 4/1963 | Turetzky | 546/285 |
| 4,648,994 | 3/1987 | Müller et al. | 552/244 |
| 4,767,573 | 8/1988 | Müller et al. | 552/244 |

FOREIGN PATENT DOCUMENTS

| | | |
|---|---|---|
| 2713575 | 10/1978 | Fed. Rep. of Germany . |
| 1352537 | 1/1964 | France . |
| 56-42631 | 10/1981 | Japan . |
| 1239778 | 7/1971 | United Kingdom . |

OTHER PUBLICATIONS

*Chemical Abstracts,* vol. 83, 1975, No. 81233s, Columbus, Ohio.

*Primary Examiner*—Richard L. Raymond
*Assistant Examiner*—Raymond Covington
*Attorney, Agent, or Firm*—Oblon, Spivak, McClelland, Maier & Neustadt

[57] ABSTRACT

1-Amino-2-bromo-4-hydroxy-anthraquinone (I)

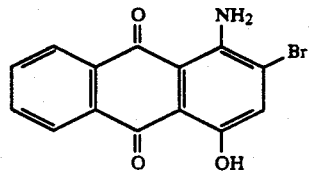

is prepared by brominating 1-amino-4-hydroxyanthraquinone (II)

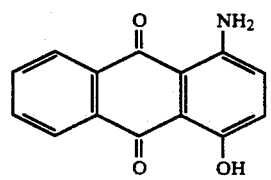

in an inert aprotic organic liquid.

3 Claims, No Drawings

PREPARATION OF 1-AMINO-2-BROMO-4-HYDROXYANTHRAQUINONE

The present invention relates to a novel process for preparing 1-amino-2-bromo-4-hydroxyanthraquinone (I)

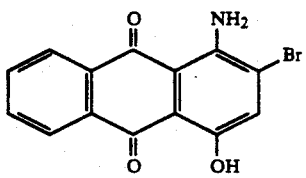

by brominating 1-amino-4-hydroxyanthraquinone (II)

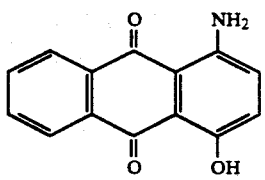

DE-A-2,713,575 describes the preparation of (I) starting from 1-aminoanthraquinone by first converting the starting compound in a sulfuric acid medium with bromine into 2,4-dibromoanthraquinone, which is then hydrolyzed with boric acid.

According to GB-A-1,239,778, the halogenation of anthraquinone derivatives is carried out in the presence of mixtures of monohydric alcohols and inert organic liquids. However, in-house experiments have shown that under these conditions bromination is only a side reaction.

JP-A-042,631 describes the halogenation of the mineral acid salts of (II) in inert organic solvents. However, this process is less selective in respect of monobromination, and it has been found to give (I) in less purity and in yields of only 70-80%.

It is an object of the present invention to remedy the defects of the existing processes in respect of purity and yields.

We have found that this object is achieved by a novel process for preparing 1-amino-2-bromo-4-hydroxyanthraquinone (I) by brominating 1-amino-4-hydroxyanthraquinone (II) in an inert aprotic organic liquid.

1-Amino-4-hydroxyanthraquinone (II) is known and obtainable in a known manner, for example by reacting 1,4-diaminoanthraquinone with manganese dioxide in sulfuric acid. For most purposes it is sufficient to use (II) in technical grade purity (about 95% strength by weight).

The starting compound (II) is suspended in the inert organic liquid. A suitable inert aprotic organic liquid is any such compound which itself is substantially unreactive under the reaction conditions. The preference is for monoaromatics substituted by electron-withdrawing groups, for example nitrobenzene, o-dichlorobenzene, trichlorobenzene and methyl benzoate.

The amount of inert organic liquid is in general from 4 to 12, preferably from 6 to 9, kg per kg of (II).

The brominating agent used is phosphorus tribromide, phosphoryl bromide, phosphorus pentabromide or in particular elemental bromine. It is in general used in a stoichiometric amount, but it may also be used in an excess of 20 equivalent %. A larger excess is not advisable in relation to the workup of the reaction mixture.

In general, the reaction is carried out at from 100 to 180° C, preferably at from 120 to 140° C.

The process comprises in general introducing a suspension of (II) in the organic phase first and adding the brominating agent at the reaction temperature. If desired, the temperature may be increased further in the course of the reaction.

Conveniently, the reaction is carried out under atmospheric pressure, but it is also possible to carry it out in a closed system under autogenous pressure.

The reaction may also be carried out continuously, for example in a stirred tank cascade, in a conventional manner.

The course of the reaction is advantageously monitored by thin layer chromatography. Once starting compound (II) is only present in traces, the reaction mixture is advantageously cooled down to about 25° C. and then worked up in a conventional manner for the product, for example by precipitating the product from the organic solution by means of methanol. The precipitated solid is filtered off and washed with methanol and water. In general it contains 90–98% by weight of (I). The purity can be determined in a conventional manner by chromatography and photometry.

1-Amino-2-bromo-4-hydroxyanthraquinone (II) is an important intermediate in the preparation of anthraquinone dyes, for example Disperse Red 60 and Disperse Red 91.

The process according to the present invention provides (I) in excellent purity and yield.

EXAMPLE 1

30 g of 1-amino-4-hydroxyanthraquinone (95% pure by weight) were suspended in 250 g of nitrobenzene, and the suspension was heated to 100° C. After 22 g of bromine had been added dropwise in the course of 15 minutes, the temperature of the reaction mixture was raised to 130–140° C. in the course of one hour and maintained at that level for 3 hours. The reaction mixture was then cooled down to 25° C, and 150 g of methanol were added. The precipitated product was filtered off, washed with 150 g of methanol and then with water, and subsequently dried.

This gave 38.6 g of a product containing 97.1% of (I), which corresponds to a yield of 98.9%.

EXAMPLE 2

30 g of 1-amino-4-hydroxyanthraquinone (95% pure by weight) were suspended in 250 g of methyl benzoate, and the suspension was heated to 110-120° C. 22 g of bromine were then added dropwise in the course of 15 minutes.

The reaction mixture was then heated to 130–140° C. and maintained at that temperature for 3 hours. It was then cooled down to 25° C, and 250 g of methanol were added. The precipitated product was filtered off, washed first with 250 g of methanol and then with water, and dried.

This gave 36.9 g of a product containing 98.2% of (I), which corresponds to a yield of 95.5%.

I claim:
1. A process for preparing 1-amino-2-bromo-4-hydroxyanthraquinone (I)

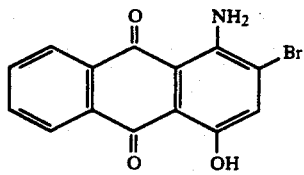 (I)

by brominating 1-amino-4-hydroxyanthraquinone (II)

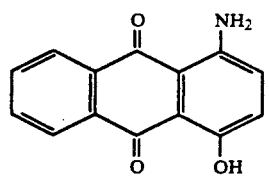 II at a temperature of from 100–180° C. in a solvent consisting essentially of an inert aprotic organic liquid.

2. A process as claimed in claim 1, wherein the inert aprotic organic liquid used is nitrobenzene, o-dichlorobenzene, trichlorobenzene or methyl benzoate.

3. The process of claim 1, wherein 1-amino-4-hydroxyanthraquinone (II) is brominated by at least one compound selected from the group consisting of phosphorus tribromide, phosphoryl bromide, phosphorus pentabromide or bromine.

* * * * *